(12) United States Patent
Birkel

(10) Patent No.: US 6,309,214 B2
(45) Date of Patent: Oct. 30, 2001

(54) METHOD OF AND APPARATUS FOR LIGATING ORTHODONTIC APPLIANCES

(76) Inventor: John W. Birkel, 10700 N. 46th St., #A-350, Tampa, FL (US) 33617

( * ) Notice: Subject to any disclaimer, the term of this patent is extended or adjusted under 35 U.S.C. 154(b) by 0 days.

(21) Appl. No.: 09/766,386

(22) Filed: Jan. 19, 2001

Related U.S. Application Data

(63) Continuation of application No. 09/584,649, filed on May 31, 2000, now Pat. No. 6,203,318, which is a continuation of application No. 09/398,673, filed on Sep. 17, 1999, now Pat. No. 6,071,120.

(51) Int. Cl.$^7$ .................................................. A61C 3/00
(52) U.S. Cl. .................................................. 433/15; 433/22
(58) Field of Search ................................ 433/13, 15, 18, 433/22

(56) References Cited

U.S. PATENT DOCUMENTS 4,867,679 * 9/1989 Rackley .................................. 433/15
5,613,853 * 3/1997 Chasan et al. ........................ 433/215

* cited by examiner

Primary Examiner—Nicholas D. Lucchesi
(74) Attorney, Agent, or Firm—Michael A. O'Neil

(57) ABSTRACT

A ligature for securing an orthodontic bracket to an orthodontic archwire is formed from nylon and comprises a thin, elongate member having sufficient tensile strength to withstand orthodontic forces. A locking member receives the ligature therethrough and prevents disengagement of the ligature from an orthodontic bracket and an orthodontic archwire following installation. In one embodiment the ligature has locking teeth at one end and a locking member at the other end for cooperation with the locking teeth to prevent disengagement of the ligature. In another embodiment the ligature has locking teeth at both ends which engage one another and a locking tube to prevent disengagement of the ligature. In another embodiment the locking member is initially open and is closable to secure the ligature therein, thereby preventing disengagement of the ligature from an orthodontic bracket and an orthodontic archwire following installation.

2 Claims, 9 Drawing Sheets

METHOD OF AND APPARATUS FOR LIGATING ORTHODONTIC APPLIANCES

This application is a continuation of Ser. No. 09/584,649, filed May 31, 2000, now U.S. Pat. No. 6,203,318, which is a continuation of Ser. No. 09/398,673 filed Sep. 17, 1999, now U.S. Pat. No. 6,071,120.

TECHNICAL FIELD

This invention relates generally to ligation techniques useful in the 3 of othodontia, and more particularly to a method of and apparatus for ligating orthodontic brackets to orthodontic archwires which is both easy and economical to use, while at the same time providing comfort to patients.

BACKGROUND AND SUMMARY OF THE INVENTION

Although the practice of orthodontics can be traced back at least to the time of the Egyptian mummies, modern development in the art began in the 1920's when Dr. Edward Angle developed the first edgewise bracket. Such a bracket is for the purpose of connecting an orthodontic archwire to a tooth, as opposed to simply wrapping wires around the tooth and ligating to an activating archwire as had been the practice previously. Later on the so-called twin bracket to apply a greater rotating and torquing force to the tooth. Still later developments included the Lewis gull wing bracket, the Steiner spring wing bracket, and the Lang stiff wing which incorporated a hole for ligating to rotate the booth.

Brackets for orthodontic use were originally had made from gold. In the late 1930's brackets machined from stainless steel were introduced. Stainless steel is generally satisfactory as an orthodontic bracket material, but presents numerous problems. First, it has traditionally been necessary to individually machine each bracket. This is costly, and also results in highly angular edge surfaces which are very uncomfortable for the patient. Another difficulty involved the distinctive appearance of stainless steel, which many patients find objectionable.

In an attempt to overcome the foregoing and other difficulties, plastic orthodontic brackets were introduced. Plastic brackets can be fabricated so as to eliminate the angular edges of machined stainless steel brackets, and are therefore more comfortable for the patient. It is also possible to make plastic brackets in almost any desired color, including highly transparent brackets. It has been found in practice, however, that the use of polycarbonate plastic orthodontic brackets presents a different set of problems. First, plastic brackets are too weak to withstand desired torquing stresses, so that breakage and failure are not uncommon. Second, in the environment of the mouth, plastic orthodontic brackets tend to rapidly discolor due to stains caused by various foods, tobacco, and beverages such as tea and coffee, etc.

The foregoing problems relating to the use of stainless steel and plastic brackets are overcome by the use of ceramic orthodontic brackets which were introduced by Dr. James M. Reynolds in the 1970's. Ceramic brackets do not have angular edges of the type associated with stainless steel brackets, and are therefore very comfortable in use. Ceramic brackets are very strong and fully capable of withstanding the forces that are applied during orthodontic procedures. Also, ceramic brackets do not discolor in use, and therefore overcome the problems associated with plastic brackets. Ceramic brackets can be highly translucent so that the color of the underlying tooth is observed through the bracket material, and in such instances ceramic brackets are nearly invisible to the eye.

Regardless of the particular material selected for the manufacture of orthodontic brackets, it is necessary to ligate or tie the bracket to an archwire extending through an archwire slot formed in the bracket. By means of appropriate and proper ligation, force is applied from the archwire to the bracket and in turn from the bracket to the tooth upon which the bracket is mounted. Such force eventually leads to the repositioning of the tooth to the desired orientation.

Orthodontic ligation has typically been accomplished utilizing stainless steel wire. Notwithstanding its widespread use, the use of stainless steel wire to ligate orthodontic brackets to archwires results in serious difficulties. First, stainless steel wires almost universally exhibit sharp ends which cause significant patient discomfort. Second, stainless steel, even in the form of small diameter wires, is highly visible in the mouth, which means that the use of stainless steel ligatures substantially reduces the aesthetic benefits deriving from the use of translucent ceramic brackets.

In order to overcome the foregoing difficulties with stainless steel ligatures, plastic O-rings have been used to ligate orthodontic brackets to archwires. U.S. Pat. No. 4,038,753, granted to Klein on Aug. 2, 1977, discloses such a plastic O-ring ligature. U. S. Patent No. 4,217,686, granted to Dragan on Aug. 18, 1980, discloses a ligator useful in conjunction with plastic O-rings to ligate orthodontic brackets to archwires.

Although overcoming the difficulties long since associated with stainless steel ligatures, the use of plastic O-rings to effect orthodontic ligation present its own set of problems. First, the injection molding process which is utilized in the manufacture of plastic O-rings is incapable of maintaining tolerances sufficiently to assure that O-ring ligatures that are nominally the same size can be relied upon to apply the same force. Additionally, and similarly to plastic orthodontic brackets, plastic O-rings tend to stain and discolor when used within the mouth of a patient.

The present invention comprises a method of and apparatus for orthodontic ligation which overcomes the foregoing and other difficulties long since associated with the prior art. In accordance with a first embodiment of the invention, an orthodontic ligature is formed from a material having a high tensile strength which does not stain or discolor when employed within the mouth of a patient. The ligature has sufficient length to be deployed around the tie wings of an orthodontic bracket and over an archwire extending through the archwire slot of the bracket. One end of the ligature comprises and insertion end and is provided with a series of locking teeth each having a locking surface facing away from the insertion end of the ligature. The opposite end of the ligature comprises a locking end and included a locking aperture adapted to receive the insertion end of the ligature and to engage the locking surfaces of the teeth thereof to prevent disengagement of the ligature after installation.

In accordance with other aspects of the invention, the ligature is formed from nylon. This is advantageous in that nylon does not discolor or stain when utilized within the human mouth. Also, nylon can be manufactured so as to be highly translucent or the ligature of the present invention can be provided in a plurality of colors, if desired. Another advantage is that nylon is a relatively low-friction material as compared to prior art orthodontic materials.

In accordance with still other aspects of the first embodiment. the ligature comprises an elongate strip having a series of locking teeth at the insertion end and having a locking tube or cylinder at the locking end. The locking tube has an axis extending parallel to that of the ligature itself and is positioned in an offset relationship to the strip comprising the ligature. The locking tube has a locking taper at one end of thereof which engages the locking teeth of the insertion end of the ligature to prevent disengagement of the ligature after installation. The locking tube is adapted for positioning within the tie slot of an orthodontic bracket which is advantageous in that it hides the locking tube from view and also maximizes patient comfort.

In accordance with a second embodiment of the invention, a ligature is formed from nylon or other, similar materials and comprises an elongate strip having locking teeth at both ends thereof. The locking teeth are tapered in the direction of the adjacent end of the ligature and have locking surfaces facing in the opposite direction. The ends of the ligature are extended in opposite directions through a small diameter locking tube. The locking teeth of the ligature engage one another and the ends of the locking tube to secure the ligature in place. In a third embodiment of the invention, a ligature is also formed from nylon, or other, similar materials. Unlike the first and second embodiments, the ligature of the second embodiment does not employ locking teeth but instead has relatively small diameter ends. In use, the opposite ends of the ligature are extended in opposite directions through a locking sleeve which is initially open and which is crushable under the action of pliers, etc. to secure the ligature in place. Either conventional or specially designed pliers may be utilized in the practice of the third embodiment of the invention.

BRIEF DESCRIPTION OF DRAWINGS

A more complete understanding to the present invention may be had by reference to the following Detailed Description when taken in conjunction with the accompanying Drawings, in which.

DETAILED DESCRIPTION

Figure 1:
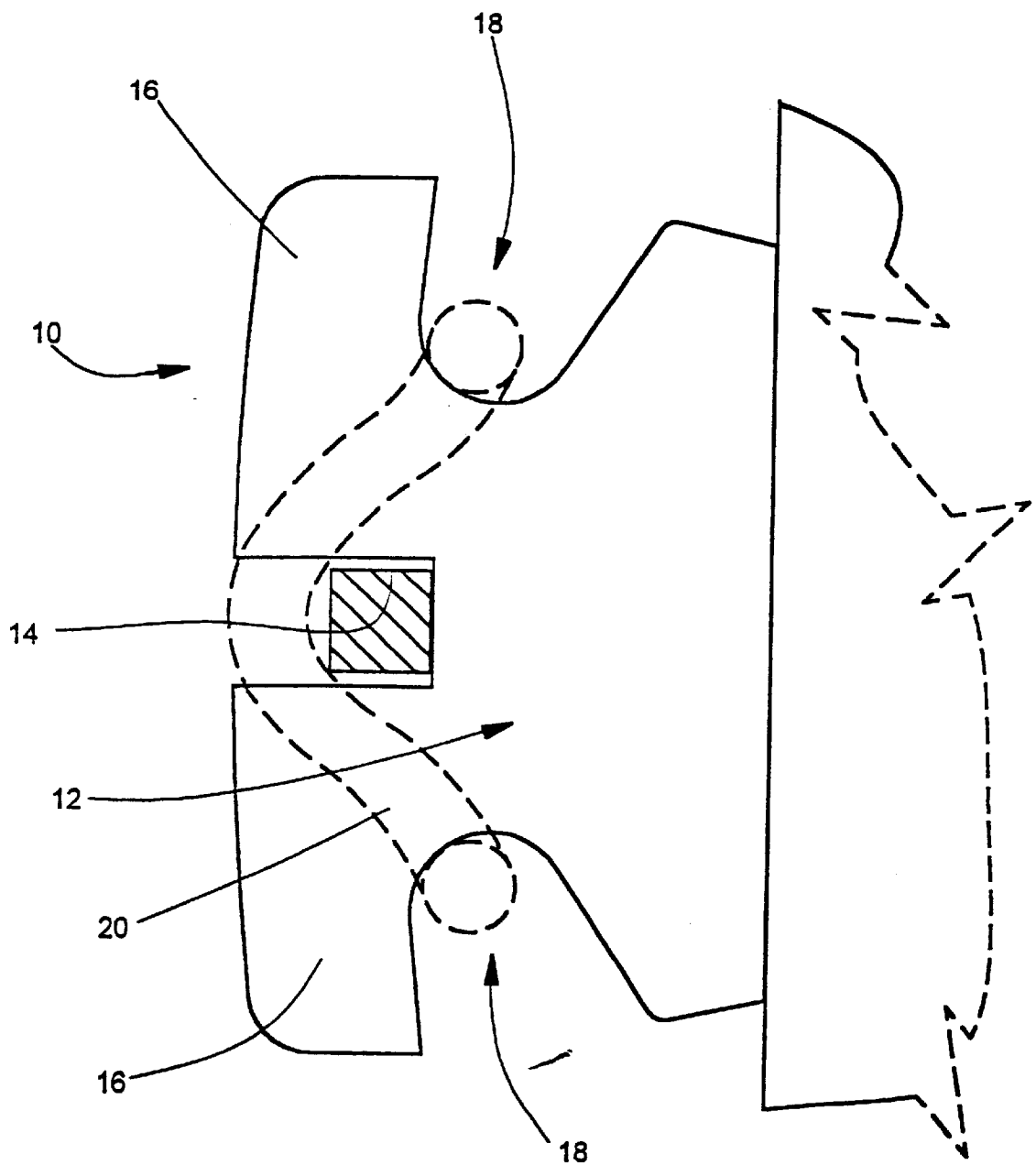
FIG. 1 is an end view of a typical orthodontic bracket.

Referring now to the Drawings, and in particular to FIG. 1 thereof, there is shown a typical orthodontic bracket 10. Those skilled in the art will appreciate the fact that the bracket 10 illustrated in FIG. 1 is illustrative of dozens if not hundreds of bracket designs which have been and are in the practice of orthodontia. The bracket 10 includes a body 12 formed from stainless steel, various plastics, various ceramics, etc. An archwire receiving slot 14 is formed in the body 12 for receiving an archwire 15 therethrough. Typically, the dimensions of the slot 14 and those of those of the archwire 15 received therein are very closely controlled.

A pair of the tie wings 16 extend outwardly on opposite sides from the archwire slot 14. A pair of ligature receiving slots 18 are located beneath the tie wings 16. A ligature 20 extends from one of the slots 18, then over an archwire 15 positioned in the slot 14, then downwardly and through the opposite slot 18, and then back and over the archwire, and then back into the original slot 18 at the point of beginning. Thus, ligature 20 functions to secure an archwire positioned in the slot 14 in engagement with the bracket 10.

Figure 2:
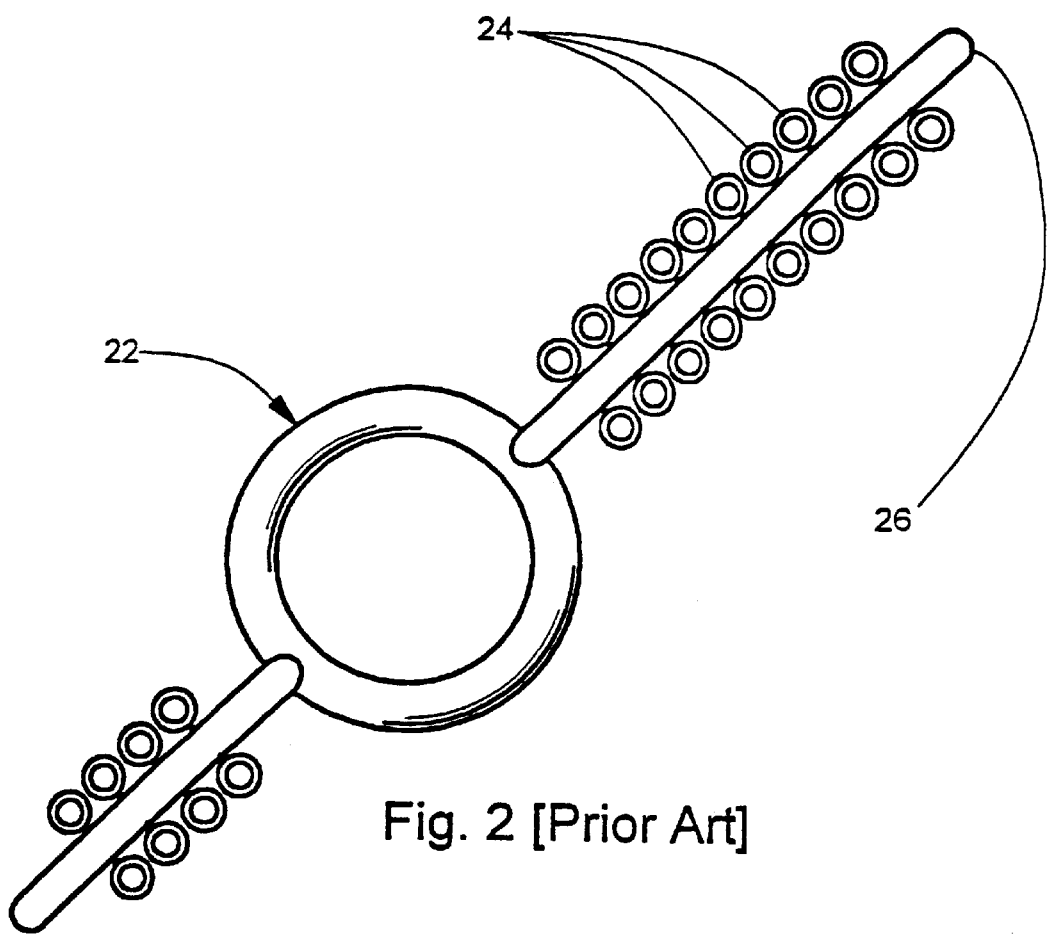
FIG. 2 is an illustration of a prior art O-ring type ligature.

FIG. 2 illustrates an injected molded construction 22 in which a plurality of plastic O-rings 24 are formed on opposite sides of a runner 26. The plastic O-rings 24 are of the type that are frequently used as ligatures in securing an archwire to an orthodontic bracket illustrated in FIG. 1. The construction and function of the O-rings 24 is further explained in U.S. Patent No. 4,038,753, granted to Klein on Aug. 2, 1997. U.S. Patent No. 4,217,686, granted to Dragan on Aug, 19, 1990, describes an appliance for installing the O-ring type ligatures illustrated in FIG. 2.

Figure 3:
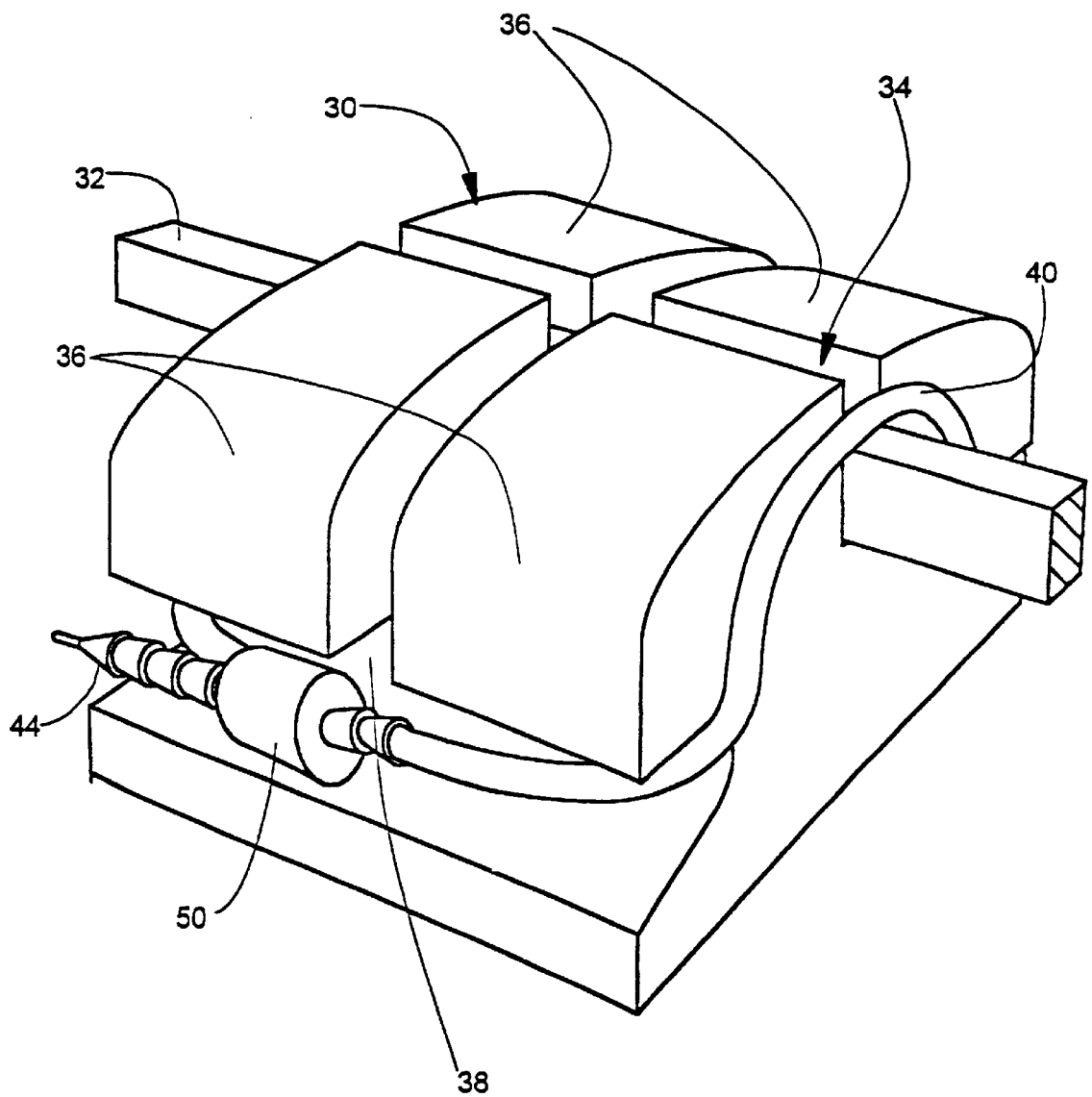
FIG. 3 is an illustration of the method ad apparatus for ligating orthodontic appliances comprising a first embodiment of the present invention.

FIG. 3 illustrates an orthodontic bracket 30 having an archwire 32 extending therethrough. The particular bracket 30 illustrated in FIG. 3 is a twin bracket. However, those skilled in the art will appreciate the fact that the present invention is equally applicable to all of the various types of orthodontic brackets which are currently in use and also those which have been used previously.

The bracket 30 has an archwire slot 34 which receives the archwire 32 and tie wings 36 extending in opposite directions form the slot 34. A ligature receiving groove 38 extends under each of the tie wings 36 for receiving a ligature therethrough. FIG. 3 further illustrates an orthodontic ligature 40 incorporating a first embodiment of the present invention.

Figure 4:
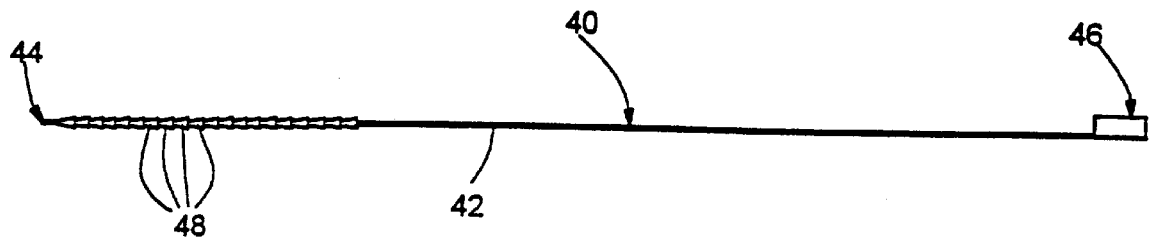
FIG. 4 is an illustration of the apparatus of FIG. 3.

FIG. 4 further illustrates the orthodontic ligature 40. The ligature 40 comprises an elongate, very slender member 42 formed from a material which has sufficient tensile strength to withstand, for an extended period of time, the forces which are utilized in the practice of orthodontia for the repositioning teeth. I n accordance with the preferred embodiment of the invention, the ligature 40 is formed from nylon, although other materials may be utilized in the practice of the invention in accordance with the requirements of particular applications thereof. The use of nylon is preferred for several reasons. First, nylon has sufficient tensile strength, even when employed in small diameter elongate members, to withstand forces of the type utilized in the practice of orthodontia. Second, nylon neither absorbs water nor stains nor discolors when utilized in the human mouth. Third, nylon may be supplied either in a highly translucent mode, or in any of a wide variety of colors as may be required by particular applications of the invention. Fourth, nylon is a low-friction material as compared to materials that have heretofore been used in orthodontic ligatures.

The ligature 40 has an insertion end 44 and a locking end 46. The insertion end 44 is provided with a plurality of locking teeth 48 each having a locking surface which faces from the insertion end 44. That is, each of the teeth 48 has a flat or blunt locking surface which faces toward the locking end 46 and away from the insertion end 44 of the ligature 40.

Figure 5:
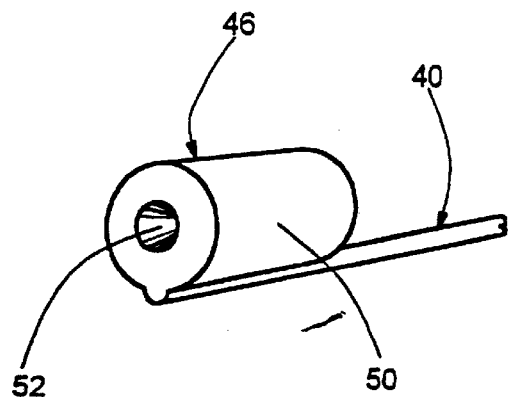
FIG. 5 is an enlargement of part FIG. 4.

Referring to FIG. 5, the locking end 46 of the ligature 40 is shown in greater detail. The locking end 46 comprises a hollow/cylinder or tube 50 adapted to receive the insertion end 44 therethrough. The tube 50 has an axis which extends parallel to the axis of the ligature 40, In actuality, the locking end 46 comprises a locking tube 50 which is secured to, positioned on, and extends parallel to the main portion of the ligature 40.

The locking end 46 of the ligature 49 comprising the locking tube 50 has a locking taper 52 at the end thereof remote from the insertion end 44. The locking taper 52 functions to receive the insertion end 44 and the locking teeth 48 therethrough while preventing reverse movement of the insertion end 44 by engagement of the locking surface of each of the locking teeth 48 with the locking taper 52. In this manner, the ligature 40 may be drawn tight but cannot be disengaged short of being cut in order to effect its release from the working position.

Figure 6:
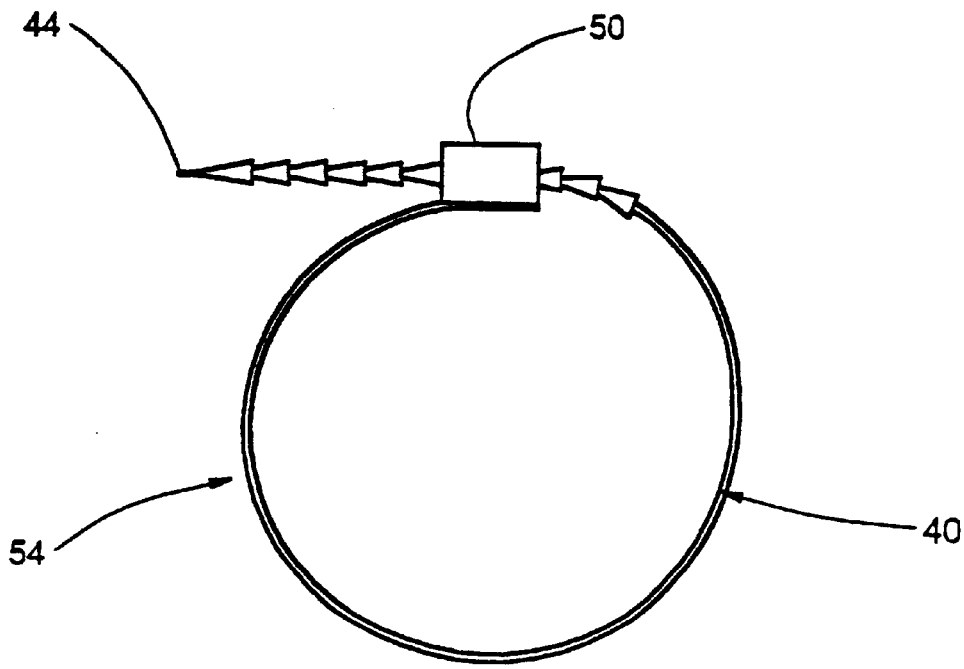
FIG. 6 is an illustration of the method of the present invention.
Figure 7:
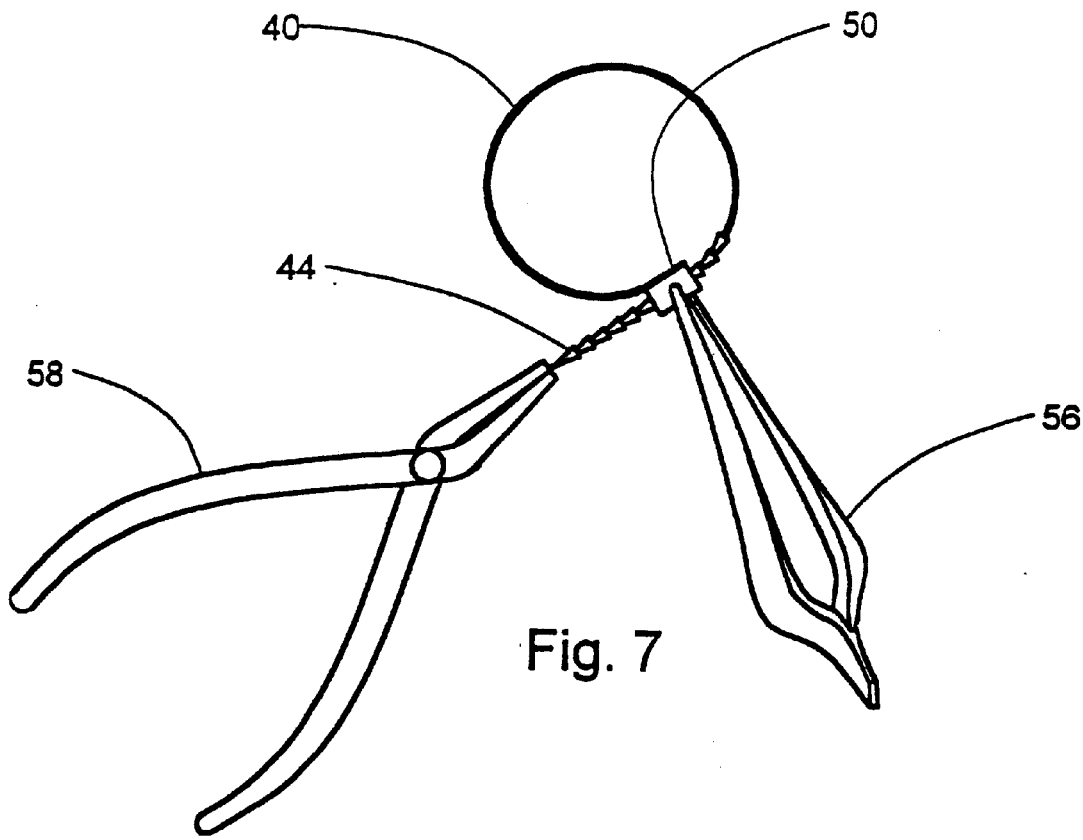
FIG. 7 is a further illustration of the method of the present invention.

The method of and apparatus for orthodontic ligature comprising the present invention are further illustrated in FIGS. 3, 6, and 7. Referring first to FIG. 6, the insertion end 44 of the ligature 40 is inserted through the tube 50 comprising the locking end 46 of the ligature 40, thereby forming a loop 54. Referring to FIG. 3, the loop 54 is positioned in the ligature receiving slot 38 on one side of an orthodontic bracket 30 and is passed over the top of the archwire 32 and into the ligature receiving groove 38 on the opposite slot of the bracket. Referring to FIG. 7, this may be accomplished by means of a pair of tweezers 56 which engage the tube 50 which comprises the locking end of the ligature 40. Next, a hemostat 58 is engaged with the insertion end 44 of the ligature 40 and is utilized to draw the insertion end 44 through the tube 50 comprising the locking end 46 of the ligature 40. As the insertion end 44 is drawn through the tube 50, the teeth 48 subsequently engage the locking taper 52. Pulling of the insertion end 44 through the tube 50 continues until sufficient tension has been established in the ligature 40 to accomplish the requisite orthodontic function as determined by the doctor utilizing the present invention.

It will be appreciated that the teeth 48 are tapered in the direction facing the insertion end 44 of the ligature 40 while comprising locking surfaces facing the locking end 46. Therefore, as each successive tooth 48 engages the locking taper 52 of the tube, the ligature 40 is retained in such position and disengagement is prevented, After the required amount of tension has been established in the ligature 40 by drawing the insertion end 44 through the tube 50, the portion of the insertion end 44 of the ligature 40 extending beyond the tube 50 is removed utilizing cutters, etc., whereupon the ligature 40 remains in place and function to secure the archwire 32 in the archwire slot 34 during the orthodontic procedure. At any convenient time as may be determined by the installing orthodontist, the ligature 40 can be removed by simply cutting and convenient portion thereof.

Referring particularly to FIG. 3, the tube 50 at the locking end 46 of the ligature 40 is preferably positioned within one of the ligature receiving grooves 38 of the bracket 30. By this means the tube 50 is blocked from view. Also, the tube 50 is prevented from causing discomfort for the patient since it is completely contained within the ligature receiving groove 38.

Figure 8:
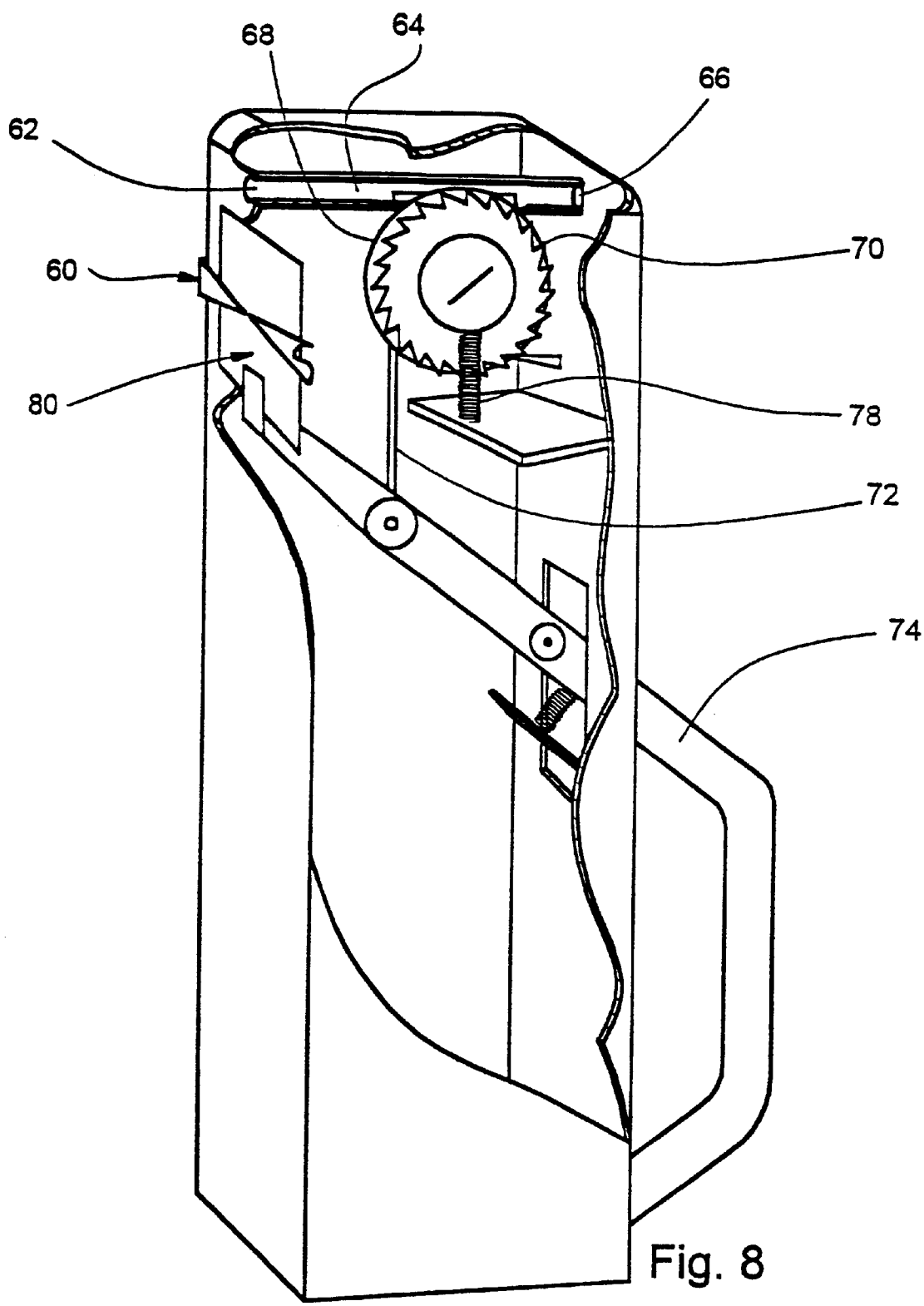
FIG. 8 is an illustration of an apparatus useful in the installation of the apparatus of FIG. 3.

Referring now to FIG. 8, there is shown an appliance 60 useful in the practice of the invention. The ligature 40 of the present invention is extended through a slot 64 and out through an exit 66. A wheel 68 provided with a suitable gear engages the locking teeth 48 of the ligature 40.

Figure 9:
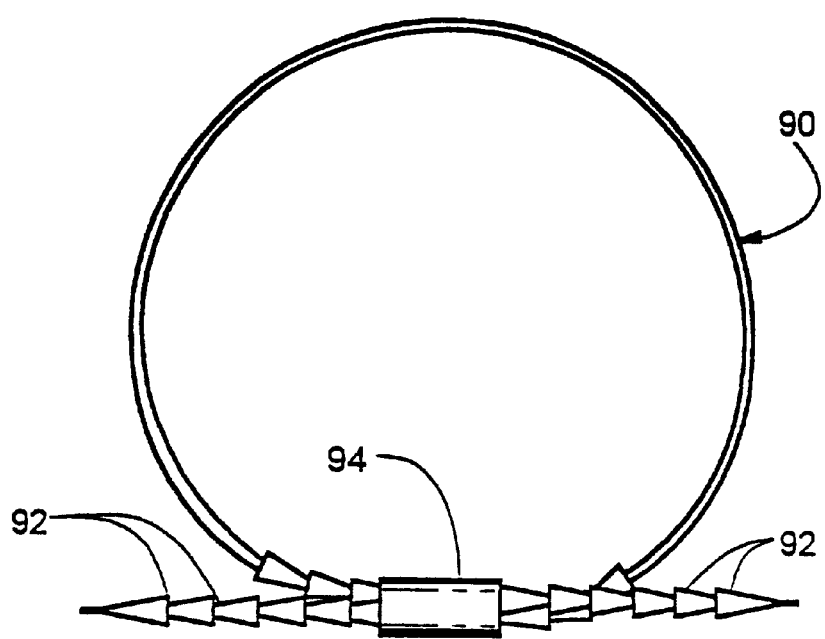
FIG. 9 is an illustration of the method and apparatus for ligating orthodontic appliances comprising a second embodiment of the present invention.
Figure 10:
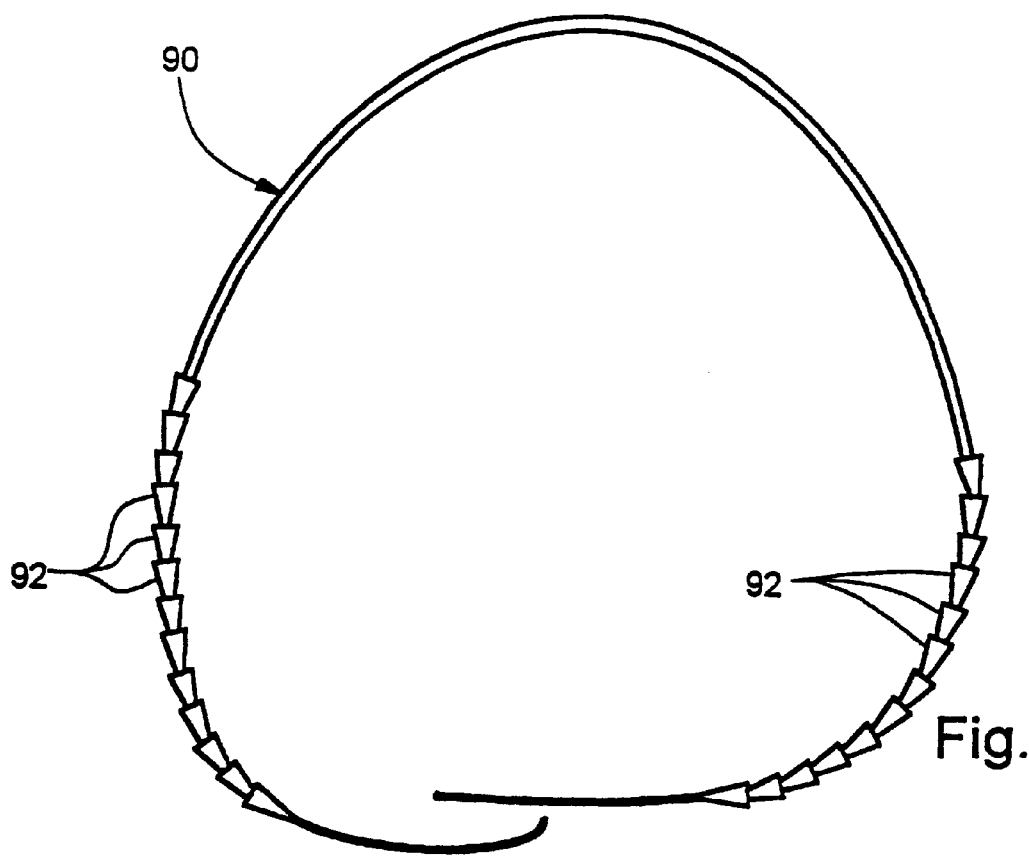
FIG. 10 is an illustration of the apparatus of FIG. 9.
Figure 11:
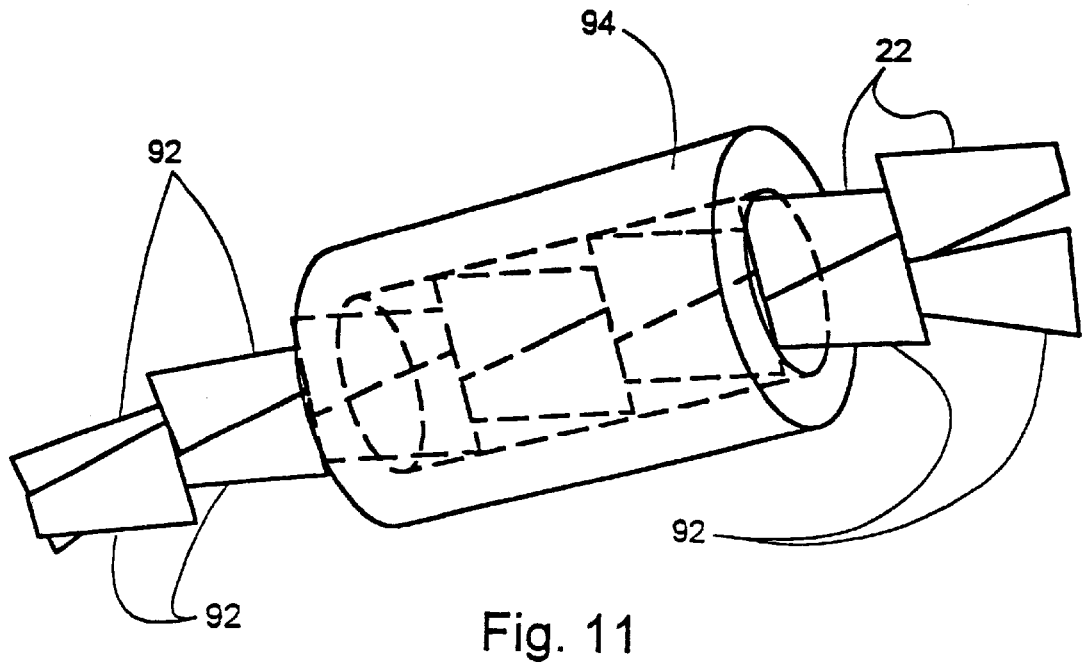
FIG. 11 is an enlargement of a portion of FIG. 9 further illustration the method and apparatus of the second embodiment of the invention.

A ratchet wheel 70 is secured to the wheel 68. A ratchet pin 72 is actuated by a handle 74 to effect actuation of the ratchet wheel and therefore the wheel 68 to move the ligature 40 through the slot 64. Reverse movement of the ratchet wheel 70 and therefore the wheel 68 is prevented by an anti-reverse pin 76. The load applied to the ligature 40 is controlled by a tension spring 78. After the required tension has been established in the ligature 40, the handle 74 is moved further inwardly, thereby actuating a cutoff blade 80 to sever the portion of the ligature 40 extending beyond the tube 50 comprising the locking end 46. FIGS. 9,10, and 11 illustrate a second embodiment of the invention. In accordance with the second embodiment, a ligature 90 is formed from nylon or other, similar materials. The ligature 90 comprises a thin, elongate strip having sufficient tensile strength to withstand the forces that are common to orthodontia. The ligature 90 differs from the ligature 40 of the first embodiment in that it is provided with locking teeth 92 at both ends thereof. In each instance the locking teeth 92 are tapered in the direction of the adjacent end of the ligature 90 and have a locking surface facing in the opposite direction.

Figure 12:
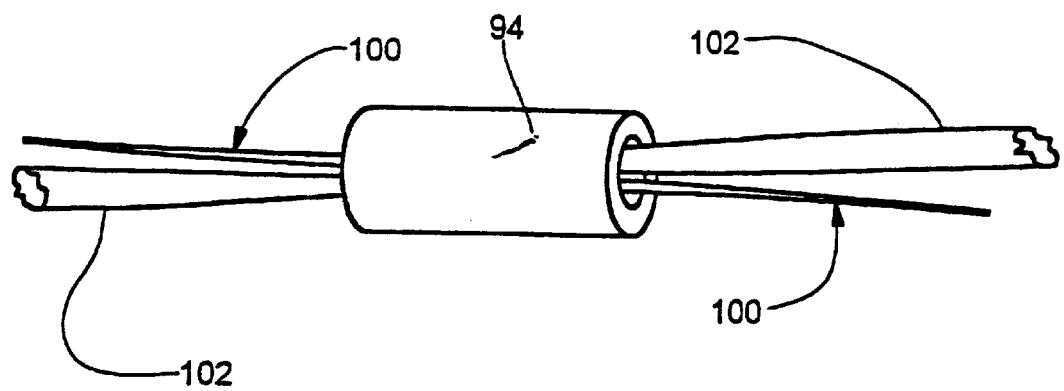
FIG. 12 is an illustration of an orthodontic ligature comprising a third embodiment of the invention.
Figure 13:
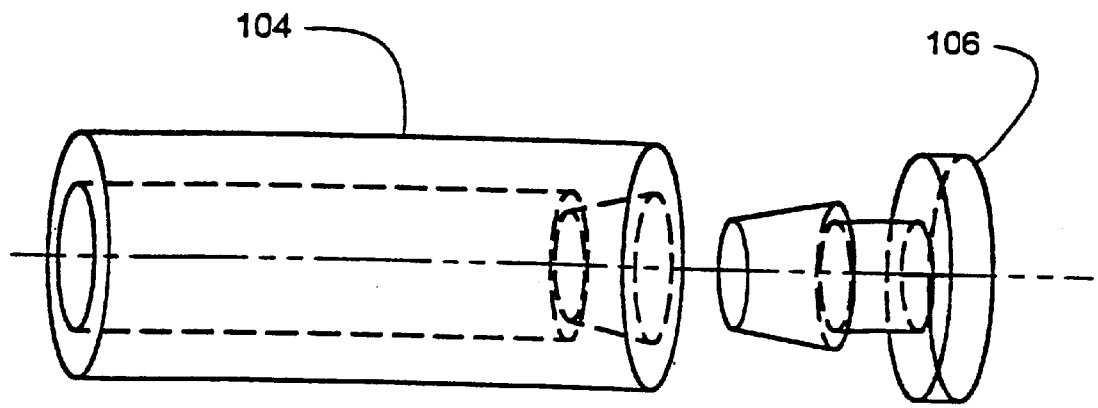
FIG. 13 is an illustration of a locking sleeve useful in the practice of the third embodiment of the invention.
Figure 14:
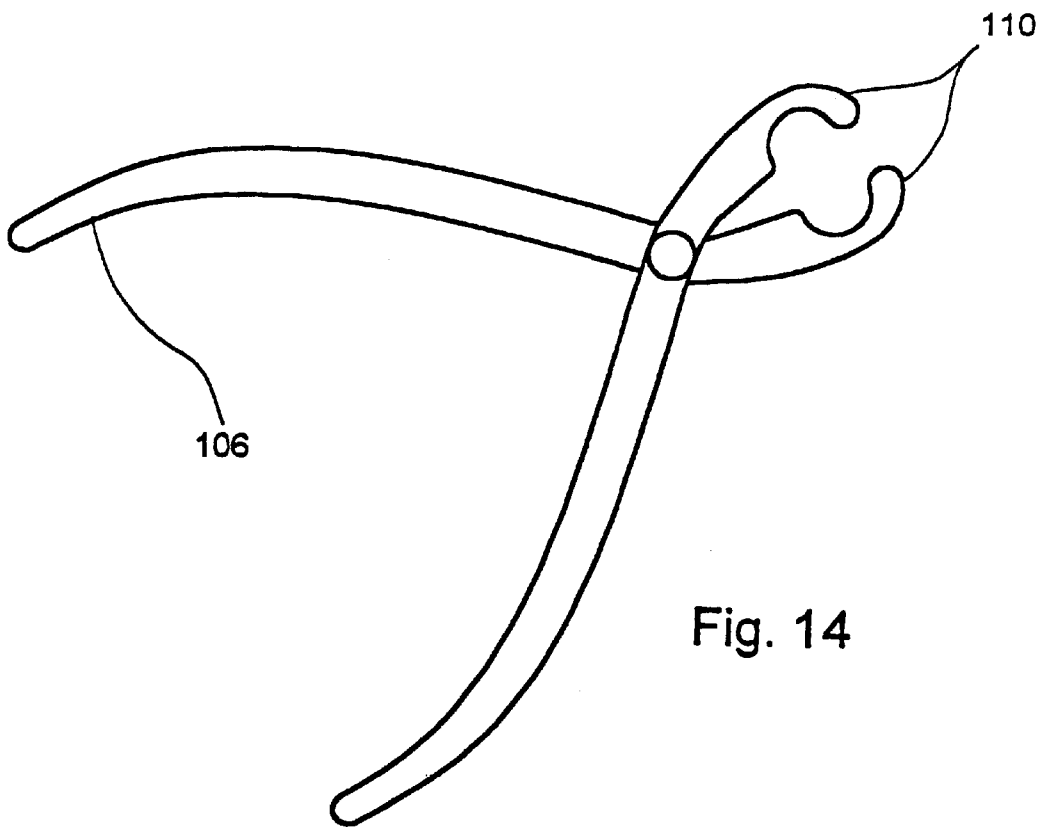
FIG. 14 is an illustration of a locking sleeve installation of FIG. 13.

FIG. 11 further illustrates the methods and apparatus of the second embodiment of the invention. The opposite ends of the ligature 90 are extended in opposite directions through a locking sleeve 94. The inside diameter of the locking sleeve 94 is closely controlled so that the opposite ends of the ligature 90 can be pulled therethrough without difficulty while assuring that the locking surfaces of the locking teeth 92 will engage one another and the end surfaces of the locking sleeve 94 to assure that the ligature 90 will remain locked in place after the desired tension has been applied thereto. FIGS. 12, 13, and 14 illustrate a third embodiment of the invention. In accordance with the third embodiment of the invention, a ligature 100 is formed from nylon or other, similar materials. The ligature 100 differs from the ligatures 40 and 90 of the first and second embodiments, respectively, in that it is not provided with locking teeth. Instead, the ligature 100 has relatively small diameter portions 102 at each end thereof. FIG. 13 illustrates a locking sleeve 104 useful in conjunction with the ligature 100 in the practive of the third embodiment of the invention. The locking sleeve 104 is initially open to allow the ends of the ligature 100 to be inserted therethrough in opposite directions. After the desired amount of tension has been applied to the ligature 100, a plug 106 is inserted into the locking sleeve 104, after which the locking sleeve 104 is crushed to secure the plug 106 and the ligature 100 in place. Alternatively, the plug 106 may be designed to snap lock into the sleeve 104 as shown.

The locking sleeve 104 may be crushed into the locked condition utilizing conventional pliers. Alternatively, the tool 108 illustrated in FIG. 14 may be utilized in conjunction with the locking sleeve 104. The tool 108 is plier-like in construction and has specially designed tips 110 which engage the locking sleeve 104 to effect crushing thereof into the locked position. If the snap lock plug alternative is used, the tool 108 is employed to retain the sleeve 104 as the plug 106 is snap locked in place.

Although preferred embodiments of the invention hae been illustrated in the accompanying Drawings and described in the foregoing Detailed Description, it will be understood that the invention is not limited to the embodiments disclosed, but is capable of numerous rearrangements, modifications, and variations of parts and elements without departing from the spirit of the invention.

What is claimed is:

1. In an orthodontic system of the type comprising an orthodontic brackett having an archwire slot, an orthodontic archwire extending through the archwire slot of the bracket, and a ligature for securing in the archwire slot, the improvement comprising:

an elongate, thin ligature having a predetermined tensile strength sufficient to withstand orthodontic forces and having an insertion end and a locking end;

the ligature having locking members at the insertion end thereof;

a ligature locking member receiver mounted at the locking end of the ligature and comprising a tubular ligature receiving passageway extending parallel to the ligature;

the locking members of the ligature for engagement with the ligature locking member receiver to secure the ligature in engagement with an orthodontic bracket and an archive extending therethrough.

2. A ligature for securing an orthodontic bracket having an archwire slot to an orthodontic archwire extending through the archwire slot of the bracket comprising:

an elongate, thin ligature having a predetermined tensile strength sufficient to withstand orthodontic forces and having opposite ends;

the ligature having locking members at one end thereof;

a ligature locking member receiver comprising a tubular ligature receiving passageway extending parallel to the ligature and located at the opposite end of the ligature from the locking members;

the locking members of the ligature for engagement with the ligature locking member receiver to secure the ligature in engagement with the orthodontic bracket and the archwire.

* * * * *

UNITED STATES PATENT AND TRADEMARK OFFICE
CERTIFICATE OF CORRECTION

PATENT NO. : 6,309,214 B2
DATED : October 30, 2001
INVENTOR(S) : John W. Birkel

It is certified that error appears in the above-identified patent and that said Letters Patent is hereby corrected as shown below:

Column 1,
Line 11, replace "useful in the 3" with -- useful in the practice --.
Line 25, add after "twin bracket" -- was developed by Swain to permit the use of the bracket --.
Line 30, replace "rotate the booth" with -- rotate the tooth --.
Line 31, replace "originally had made" with -- originally hand made --

Column 2,
Line 50, replace "comprises and insertion end" with -- comprises an insertion end --.
Line 53, replace "and included a locking" with -- and includes a locking --.
Line 65, replace "ment. the ligature" with -- ment, the ligature --.

Column 3,
Line 5, replace "of thereof which engages" with -- thereof which engages --.
Line 33, replace "understanding to the present" with -- understanding of the present --.
Line 39, replace "method ad apparatus" with -- method and apparatus --.
Line 43, replace "an enlargement of part Fig. 4" with -- an enlargement of part of Fig. 4 --.
Line 56, replace "illustration the method" with -- illustrating the method --.
Line 63, replace "of FIG. 13" with -- tool useful in conjunction with the locking sleeve of FIG. 13. --

Column 4,
Line 3, replace "which have been and are in" with -- which have been and are in use in --.
Line 8, replace "and those of those" with -- and those --.
Line 28, replace "Aug, 19, 1990" with -- Aug. 19, 1980 --.
Line 40, replace "form the slot 34." with -- from the slot 34 --.
Line 50, replace "repositioning teeth" with -- repositioning of teeth --.

Column 5,
Line 1, replace "surface which faces" with -- surface which faces away --.
Line 13, replace "ligature 49" with -- ligature 40 --.
Line 30, replace "receiving slot 38" with -- receiving groove 38 --.
Line 40, replace "subsequently engage the" with -- sequentially engage the --.
Line 50, replace "taper 52 of the tube," with -- taper 52 of the tube 50, --.
Line 60, replace "cutting and convenient" with -- cutting any convenient --.

UNITED STATES PATENT AND TRADEMARK OFFICE
CERTIFICATE OF CORRECTION

PATENT NO. : 6,309,214 B2
DATED : October 30, 2001
INVENTOR(S) : John W. Birkel

It is certified that error appears in the above-identified patent and that said Letters Patent is hereby corrected as shown below:

Column 6,
Line 45, replace "in the practive of" with -- in the practice of --.
Line 63, replace "of the invention hae" with -- of the invention have --.

Column 7,
Line 5, replace "orthodontic brackett having" with -- orthodontic bracket having --.

Column 8,
Line 2, replace "an archive extending" with -- an archwire extending --.

Signed and Sealed this

Sixteenth Day of July, 2002

*Attest:*

*Attesting Officer*

JAMES E. ROGAN
*Director of the United States Patent and Trademark Office*